United States Patent [19]
Dempo

[11] Patent Number: 5,512,178
[45] Date of Patent: Apr. 30, 1996

[54] WATER TREATMENT METHOD AND APPARATUS THEREFOR

[75] Inventor: Fumio Dempo, Saitama, Japan

[73] Assignees: Yoshihisa Masuda; Shiroh Shimaya, both of Japan; part interest to each

[21] Appl. No.: 406,782

[22] Filed: Mar. 20, 1995

Related U.S. Application Data

[63] Continuation of Ser. No. 907,535, Jul. 2, 1992, abandoned.

[30] Foreign Application Priority Data

Apr. 17, 1992 [JP] Japan ..................................... 4-122944

[51] Int. Cl.$^6$ ....................................................... C02F 9/00
[52] U.S. Cl. .......................... 210/638; 210/652; 210/668; 210/669; 210/748; 210/760; 210/96.1; 210/182; 210/195.2; 210/202; 210/258; 210/259; 210/266; 210/900
[58] Field of Search ..................................... 210/638, 652, 210/662, 663, 669, 748, 760, 96.1, 192, 202, 259, 266, 900, 668, 96.2, 182, 195.2, 258

[56] References Cited

U.S. PATENT DOCUMENTS

| | | | |
|---|---|---|---|
| 3,870,033 | 3/1975 | Faylor et al. | 210/900 |
| 4,548,716 | 10/1985 | Boeve | 210/760 |

*Primary Examiner*—Ivars Cintins
*Attorney, Agent, or Firm*—Michael D. Bednarek; Marks & Murase

[57] ABSTRACT

In a water treatment method and an apparatus therefor, a high purification step comprising a precision filter and an ion-exchange resin is added to a treatment system having ozone supply units, filtering units and an ultraviolet-ray irradiating unit. Treatment objective water is treated by an ozone supply unit, a filtering unit and an ultraviolet-ray irradiating unit, so as to be brought to clean water. The clean water is treated, in super pure water, by the high purification step, and an amount of dissolved oxygen is reduced. The clean water can flow out to a location on the outside of the treatment system, from a final step, as super pure water or potable water which can immediately be used.

37 Claims, 3 Drawing Sheets

WATER TREATMENT METHOD AND APPARATUS THEREFOR

This application is a continuation of application Ser. No. 07/907,535 filed Jul. 2, 1992, now abandoned.

BACKGROUND OF THE INVENTION

The present invention relates to a water treatment method and an apparatus therefor which are suitable for use where treatment objective water is treated in purification to produce super pure water, potable water and the like, or for use where seawater is treated in desalination.

It has been known that, if ozone is utilized to purify treatment objective water, a strong oxidation and sterilization action of the ozone makes it possible to remove contamination due to, particularly, organic substances. For this end or purpose, however, it is required that a plenty of ozone gases high in concentration is mixed with the treatment objective water. Since the ozone is apt to be immediately changed to oxygen. In addition, since a normally high water pressure is applied to a flow system which causes the treatment objective water to flow, it is extremely difficult to practically mix the plenty of ozone gases with and into the treatment objective water. Further, in spite of the fact that uses of the treatment objective water are for industry and for agriculture, it is naturally required to treat in purification a plenty of water like several tons or several ten tons per hour. However, an ozone supply apparatus which satisfies such condition is close to none at all, in the extent or range as far as the inventor of the present application knows.

In view of the above, the inventor of the present application has previously proposed an apparatus which is capable of mixing a plenty of ozone gases high in concentration into treatment objective water, on the assumption that a plenty of treatment objective water is purified (for example, reference should be made to Japanese Patent Laid-Open No. SHO 63-200891). Further, the inventor of the present application has proposed a water treatment apparatus which utilizes the above-described apparatus (for example, reference should be made to Japanese Patent Publication No. HEI 3-72359).

In a process to pursue such a technique of purifying the water, it has been possible to obtain knowledge that the technique developed by the inventor of the present application is extremely effective in obtaining super pure water and potable water, and the technique is useful also for desalination of the seawater.

Generally, in order to obtain super pure water, waterwork water, underground water, industrial water and the like are used as raw water. As will be known well, however, various impurities are contained in the water. Specifically, contained in the water are rubbish or refuse and other suspendible particles, fine particles of a silt-like material or the like, microorganisms such as bacteria and the like, and a colloidal material, as an "insoluble material", for example, and organic substances such as ion, protein and the like, soluble gasses such as oxygen/carbon dioxide gases and the like, as a "soluble material".

For the reason discussed above, in order to obtain super pure water, it is necessary to efficiently remove such impurities. Particularly, the pure water for semiconductors contains elements harmful for the semiconductors, and dislikes or hates bacteria (raw fingi or viable cells) being grown. Thus, it is required to completely remove the bacteria.

SUMMARY OF THE INVENTION

In view of the above, an object of the invention is to provide a method and an apparatus therefor in which the previously proposed water treatment apparatus is further improved, and in which a characteristic originally had by ozone, that is, functions such as sterilization, decolorization and deodorization are exhibited approximately 100%, whereby impurities in raw water are removed, including bacteria and other impurities so that super pure water and potable water can efficiently be produced, and if the treatment objective water is seawater, the seawater is efficiently desalinated.

According to the invention, there is provided a water treatment method comprising the steps of flowing treatment objective water through a treatment system having an ozone supply unit, a filtering unit and an ultraviolet-ray irradiating unit, to purify the treatment objective water; adding a high purification step having a precision filter and an ion-exchange resin, to the treatment system; treating the treatment objective water by the ozone supply unit, the filtering unit and the ultraviolet-ray irradiating unit, to form clean water; treating, in super pure water treatment, the pure water by the high purification step; reducing an amount of dissolved oxygen within the clean water; and enabling the clean water to flow to a location on the outside of the treatment system by a final step as super pure water and potable water which can immediately be used.

Further, a reverse osmosis membrane and an ultraviolet-ray irradiating unit may be added to the high purification step having the precision filter and the ion-exchange resin, to treat the treatment objective water.

Moreover, in the water treatment method according to the invention, the arrangement may be such that a desalination step having a precision filter and a reverse osmosis membrane are added to the aforesaid treatment system, and impurities are removed from the seawater and salinity is removed from the seawater, thereby treating the seawater in desalination.

Further, according to the invention, there is also provided a water treatment apparatus which is arranged such that an ozone reaction tank is added to a subsequent step of the ozone supply unit in the aforementioned treatment system, and a precision filter and an ion-exchange resin tower are added to a subsequent step of the ultraviolet-ray irradiating unit.

Furthermore, the arrangement may be such that a reverse osmosis membrane and an ultraviolet-ray irradiating unit are added in combination with these precision filter and ion-exchange resin tower.

Moreover, the water treatment apparatus according to the invention may be arranged such that, in the above-described treatment system, an ozone reaction tank is added to a subsequent step of the ozone supply unit, and a precision filter, a reverse osmosis membrane, an ultraviolet-ray irradiating unit, a precision filter, and an ion-exchange resin tower are arranged in a previous step or a subsequent step of the ultraviolet-ray irradiating unit.

Further, the water treatment apparatus according to the invention may be arranged such that a gold collecting unit is combined with a location between the precision filter and the reverse osmosis membrane, to enable gold to be collected from seawater serving as the treatment objective water.

Furthermore, the water treatment apparatus according to the invention may be arranged such that, in the aforementioned treatment system, an ozone reaction tank and a precision filter are added to a subsequent step of the ozone supply unit, and a reverse osmosis membrane and an ozone supply unit are combined with a location of a previous step of the ultraviolet-ray irradiating unit.

Moreover, the water treatment apparatus according to the invention may be arranged such that an ozone supply unit, an ozone reaction tank, a filtering unit, a precision filter, an ozone supply unit, a filtering unit, a precision filter, a reverse osmosis membrane, an ozone supply unit, a precision filter and an ultraviolet-ray irradiating unit are successively combined with the aforesaid treatment system, so that the water treatment apparatus is brought to an apparatus suitable for desalination.

With the arrangement of the invention, the treatment objective water is first treated in clean water (pure water) by a purification step. The treatment objective water is passed through the ozone supply unit at a previous step of a treatment system. At the ozone supply unit, ozone gas high in concentration is supplied to the treatment objective water. Oxidation sterilization, decolorization and deodorization due to the ozone are applied to the treatment objective water by the ozone supply unit and the ozone reaction tank combined with a subsequent step of the ozone supply unit, to sterilize bacteria and other microorganisms and to decompose protein and other organic matters or substances.

The ozone treatment exhibits sufficient advantages at the ozone reaction tank which is combined with the subsequent step of the ozone supply unit. In the treatment system, the ozone supply unit and the ozone reaction tank are arranged in plural so that the treatment objective water is repeatedly purified by the ozone. The treatment objective water is filtered at a filtering step which is arranged between the plurality of ozone treatment steps.

An inorganic-substance filtering unit and an activated-carbon filtering unit are utilized as the filtering unit. The filtering units beforehand remove inorganic substances in the treatment objective water, and absorb and remove oxidizing materials and organic substances, to perform a role or function of protecting the precision filter and the reverse osmosis membrane which are arranged in a subsequent step of the treatment system. Then, the treatment objective water passes through the ultraviolet-ray irradiating unit so that bacteria are sterilized and the organic substances are decomposed and treated by irradiation of ultraviolet rays. At this stage, the treatment objective water is already purified at a considerably high level and is brought to clean water (pure water).

Subsequently, at the subsequent high purification step, the super-pure-water treatment is applied to the above-described clean water (pure water). The clean water (pure water) purification(pure water-)treated in the previous purification step passes through the precision filter and the ion-exchange resin tower added to a subsequent seep of the ultraviolet-ray irradiating unit, whereby the super-pure-water treatment is applied to the clean water (pure water).

The precision filter is one which removes impurities equal to or less than 1 μm within the clean water. The residue or residuum of the bacteria and the organic substances which have been sterilized and decomposed by the previous ultraviolet-ray irradiating unit is removed without exception. The ion-exchange resin tower removes the ion in the clean water to complete the super-pure-water treatment. The precision filter and the ion-exchange resin tower achieve the super-pure-water treatment by the synergism with the ozone supply unit, the filtering unit, the ultraviolet-ray irradiating unit and the like, which are other units.

By the way, the present invention intends to dissolve a plenty of ozone gases high in concentration, into water by the ozone supply unit, to execute purification treatment. Accordingly, there is a case where an amount of dissolved oxygen within the clean water is considerably high so that a small amount of ozone remains even if the clean water reaches a subsequent stage of the treatment system. In view of this, providing against case where the clean water is used as potable water as soon as possible, the clean water passes through the ion-exchange resin tower to zero the amount of dissolved oxygen in the clean water without a break.

In case where polluted or contaminated water rich in impurities is purified as treatment objective water, or in case where industrial water, underground water or waterwork feed water is purified to produce super pure water for semiconductors, the water is treated by the highly high purification step in which the above-described high purification step is further improved or developed.

The highly high purification step is a step in which the reverse osmosis membrane and the ultraviolet-ray irradiating unit are combined with the aforesaid precision filter and ion-exchange resin tower. Almost all of the ion, fine particles, bacteria and other impurities, which may pass through the aforementioned precision filter, is almost removed by the reverse osmosis membrane. If the treatment objective water is seawater, salinity in the seawater is removed at the highly high purification step, and desalination treatment is applied to the treatment objective water.

The ultraviolet-ray irradiating unit further sterilizes bacteria which may be removed by the reverse osmosis membrane, and decomposes organic substances. A precision filter, which is similar to that described previously, is arranged at a subsequent step of the ultraviolet-ray irradiating unit, to remove the residue or residuum without exception. The treatment objective water lastly passes through the ion-exchange resin tower, to remove ion similarly to the above. It is possible to easily obtain potable water by the highly high purification treatment to make it double sure, even if contaminated water rich in impurity is made to the treatment objective water. Further, it is possible to easily produce super pure water for semiconductors, from the industrial water, the underground water or the waterwork feed water. Moreover, it is possible to purify seawater to produce fresh water.

Furthermore, in case where the gold collecting unit is combined with a location between the precision filter and the reverse osmosis membrane, it is possible to collect gold from seawater.

As described above, according to the water treatment method and the water treatment apparatus therefor of the invention, the arrangement is as follows. That is, the treatment objective water is pretreated at the purification step mainly comprising the ozone supply unit, the filtering unit and the ultraviolet-ray irradiating unit, so as to be brought to clean water. It is possible to treat, in super pure water, the clean water by the high purification step combined with the purification step, or by the highly high purification step. The high purification step comprises the precision filter and the ion-exchange resin. The highly high purification step comprises the reverse osmosis membrane and the ultraviolet-ray irradiating unit which are further added to the precision filter and the ion-exchange resin. Particularly, the function of the ozone is sufficiently utilized and, in addition thereto, efficient water treatment can be achieved by the synergism of the various utilized units. Further, it is possible to effectively produce the potable water, the super pure water, or the super pure water for semiconductors without selection of types of treatment objective water. Furthermore, if the treatment objective water is seawater, it is possible to desalination-treat the seawater. Accordingly, there are produced superior advantages that many uses can be expected in addition to the normal or usual uses, in case where potable water for human beings is secured from water polluted by typhoon or other reasons, in case where agricultural chemicals are removed from agricultural water and the water is reused, in case where portable water is desired to be produced from seawater at an area where there is less In an amount of rainfall per year so that secureness of the potable water is difficult, and the like.

DESCRIPTION OF THE EMBODIMENTS

Figure 1:
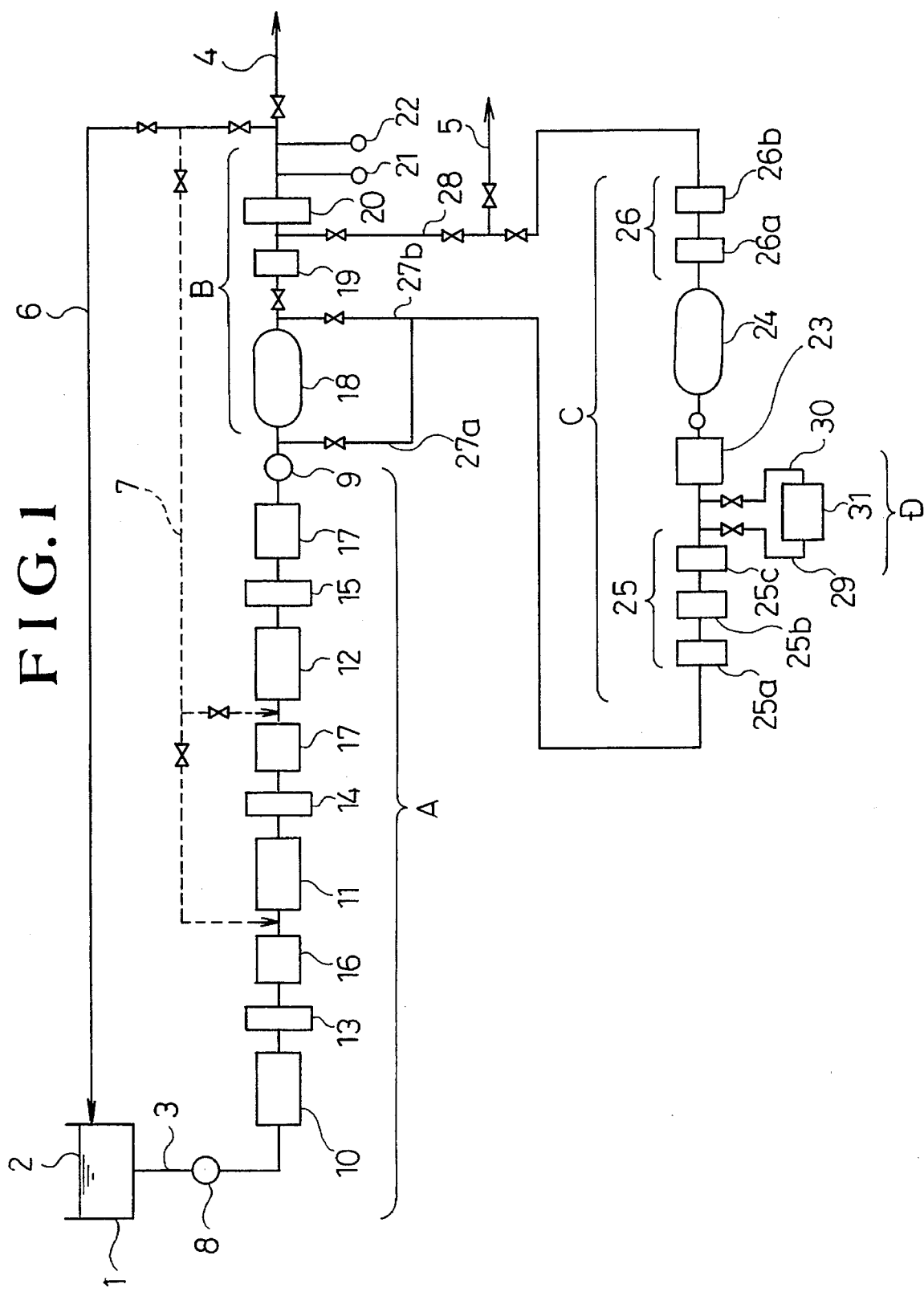
FIG. 1 is a view of entire steps, showing a first embodiment of a water treatment apparatus.

Various embodiments will be described below with reference to the accompanying drawings. In this connection, for convenience of the description, the description will be made centering around a "water processing or treatment apparatus" with reference to the drawings, and reference will be made to the contents of a "water treatment method" as occasion demands.

The water treatment apparatus comprises a water tank 1 which is filled with treatment objective water (raw water) 2. Connected to the water tank 1 are a treatment system leading to a purifying step A and a high purifying step B, and a treatment system leading to the purifying step A and a highly high purifying step C. Associated with or combined with the highly high purifying step C is a step D of collecting gold.

A water flow pipe 3, by which the above-described various steps are connected to each other, has, at its terminal or end, a pair of outflow portions 4 and 5. Further, as occasion demands, connected to the water flow pipe 8 are a recirculation water flow pipe 6 for recirculating water after treatment to cause the water to flow into the water tank 1, and a retreatment water flow pipe 7 for returning the water after treatment to a location on the way of the treatment system. A first pump 8 and a second pump 9 are arranged in the water flow pipe 3 so that an adequate hydraulic or water pressure is applied to the entirety of the water flow pipes 3, 6 and 7.

The details of the purifying step A will be described.

The purifying step A comprises first, second and third ozone supply units 10, 11 and 12 arranged in multiple steps as "an ozone supply device", first, second and third ozone reaction tanks 13, 14 and 15 associated respectively with subsequent steps of the respective first, second and third ozone supply units 10, 11 and 12, an inorganic filtering unit 16 and an activated-carbon filtering unit 17 arranged as "a filtering device", and an ultraviolet irradiation unit (a first ultraviolet irradiation unit) 18. The purifying step A purifies the treatment objective water 2 to form purified water (demineralized or pure water).

The ozone supply units 10, 11 and 12 and the ozone reaction tanks 13, 14 and 15 are capable of injecting a plenty of ozone gases high in concentration into high-pressure and high-speed water flow (treatment objective water 2) within the water flow pipe 3. In this connection, an ozone supply unit previously proposed by the inventor of the present application (for example, refer to Japanese Patent Laid-Open No. SHO 63-200891) can be used as each of the ozone supply units 10, 11 and 12. Each of the ozone reaction tanks 13, 14 and 15 is provided for so-called "bringing strength to the ozone", and provides an environment in which the ozone injected into the treatment objective water 2 exhibits sufficient sterilization, decolorization and deodorization functions of the water.

The inorganic filtering unit 16 uses a sand filtering unit, for example. The activated-carbon filtering unit 17 has an adequate combination of a petroleum system, a coal system and a coconut-husk system large or high in a reduction force. The inorganic filtering unit 16 executes settling and removal of inorganic and organic matters within the treatment objective water 2, while the activated-carbon filtering unit 17 executes absorption and removal of oxidizers and organic matters. So-called pretreatment is applied to the treatment objective water 2 to facilitate treatment of "precision filter" and "reverse osmosis membrane" to be described subsequently, and an attempt is made to beforehand protection that, even if a plenty of treatment objective water 2 is led, clogging and blinding and reduction in treatment efficiency do not occur.

The ultraviolet irradiation unit (first ultraviolet irradiation unit) 18 performs actions of decomposing organic substances within the treatment objective water 2 and sterilizing bacteria.

The high purifying step B will be described.

The high purifying step B combined with the above-described purifying step A principally comprises a precision filter 19 and an ion-exchange resin tower 20. The precision filter 19 intends to remove impurities equal to or less than 1 μm. If there are organic substances decomposed by the aforesaid ultraviolet irradiation unit 18, bacteria sterilized thereby and other residuum or residue in the clean water, the precision filter 19 removes them. As occasion demands, a plurality of precision filters similar to the precision filter 19 are combined with each other in multiple steps or stages. The ion-exchange resin tower 20 removes ion within the water which has passed through the precision filter 19 by ion-exchange resin (strong acidic cation exchange resin or strong basic exchange resin) which is arranged within the ion-exchange resin tower 20. Further, at this time, if ozone survives within the clean water, tile ion-exchange resin tower 20 zeros the ozone.

A chromaticity meter 21 and an electric-conductivity measuring meter 22 are arranged at the outflow portion 4 which is located at the terminal of the treating system rearward of the ion-exchange resin tower 20. Consideration will be made to case where the treatment objective water 2 passes through the purifying step A and the highly purifying step B so as to be brought to super purified water, and the super purified water is taken out of the outflow portion 4 as it is as "potable water" and is used. This is preferable in viewing and confirming how the water is sterilized and purified. A person who obtains potable water by this apparatus and method will obtain a further sense of security by the use of the chromaticity meter 21 and the electric-conductivity measuring meter 22.

The highly high purifying step C will be described.

The highly high purifying step C is one which further improves or develops the aforesaid high purifying step B. The highly high purifying step C is a purifying treatment step which is preferable in case where purification is made on the treatment objective water 2 high in pollution level, in case where super purified treatment for semiconductors is executed, or in case where seawater is desalination-treated as the treatment objective water 2.

Basically, the highly high purifying step C is arranged such that a reverse osmosis membrane 23 and a ultraviolet irradiating unit (second ultraviolet irradiating unit) 24 are combined with each other at a step previous to the aforesaid precision filter 19 and ion-exchange resin tower 20. In this embodiment, however, a first filter 25a of the level of 5 μm, a second filter 25b of the level of 1 μm and a third filter 25c of the level of 0.1 to 0.6 μm are used as a plurality units of a "precision filter unit 25" which gradually or successively raises filtering function, in place of the aforesaid precision filter 19. Further, a fourth filter 26a of the level of 1 μm and a fifth filter 26b of the level of 0.1 to 0.6 μm are used as "other precision filter units 26" in a subsequent step of the ultraviolet irradiating unit 24.

In case where super pure water for semiconductors is obtained, the precision filter units 25 and 26 may be brought to "ultrafilter membranes" which are combined with the reverse osmosis membrane 23. If a filter of the level of submicron is used, it is possible to remove also colloidal materials of the level of 0.005 to 0.01 μm.

For the reverse osmosis membrane 23, a polyamide membrane is preferable. The polyamide membrane is one which removes colloidal materials, bacteria and the like such as trihalomethane that is carcinogen, particulate, ion or the like. The polyamide membrane can remove almost all of impurities in clean water (pure water) obtained by the previous purifying step A. If the treatment objective water 2 is seawater, the reverse osmosis membrane 23 removes salinity in the seawater, and applies thereto desalination treatment.

The ultraviolet irradiation unit (second ultraviolet irradiation unit) 24 is substantially similar to the aforesaid ultraviolet irradiation unit (first ultraviolet irradiation unit) 18, and is also similar in operation thereto. Thus, description of the ultraviolet irradiation unit (second ultraviolet irradiation unit) 24 will be omitted.

Such purification treatment at the highly high purification step C uses a branch pipe 27a branching the clean water after ultraviolet-ray irradiation treatment by the ultraviolet-ray irradiating unit (first ultraviolet irradiating unit) 18, at a step subsequent to the ultraviolet-ray irradiating unit (first ultraviolet-ray irradiating unit) 18, by operation of a valve provided in the water flow pipe 3, or uses a branch pipe 27b which branches the clean water at a subsequent step of the ultraviolet-ray irradiating unit (first ultraviolet-ray irradiating unit) 18, thereby leading the clean water to the precision filter 25. Further, the clean water is led to the reverse osmosis membrane 23, the ultraviolet-ray irradiating unit (second ultraviolet-ray irradiating unit) 24, and the other precision filter unit 26. The clean water passes through other branch line 28, and is led to the ion-exchange resin tower 20. Thus, the purification treatment is executed.

In connection with the above, if it is not required to treat the treatment objective water 2 by the ion-exchange resin tower 20, similarly to case where potable water is produced from the treatment objective water 2 which is not so much contaminated, the water is taken out from the another outflow portion 5 which is provided in the branch pipe 28, and may immediately be used as potable water.

The step D of collecting gold will be described.

Figure 2:
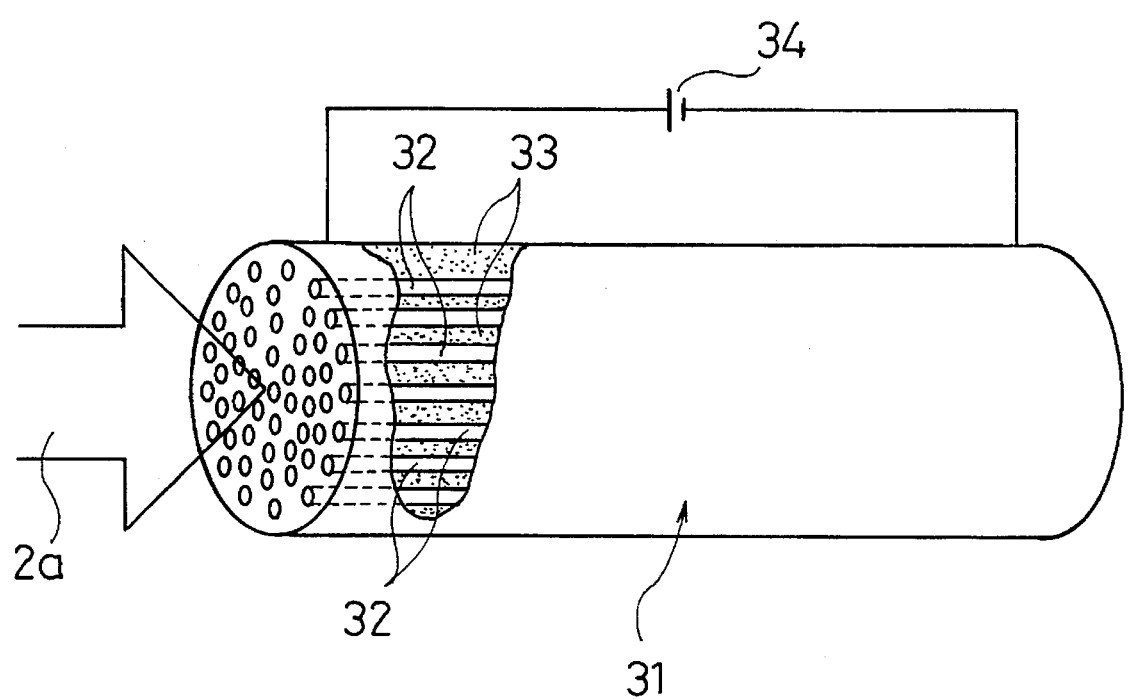
FIG. 2 is a schematic perspective view showing a unit for collecting gold, illustrated in FIG. 1.

A unit 31 for collecting gold is incorporated at a location between the precision filter unit 25 and the reverse osmosis membrane 23 in the previous highly high purification step C, through a pair of branch pipes 29 and 30 having respective operating valves thereof. As shown in detail in FIG. 2, the gold collecting unit 31 is brought to a filter configuration as a whole, and has therewithin a plurality of passage bores 32 through which seawater 2a passes. The gold collecting unit 31 has a body which is formed into a "ceramic body" with which gold powder 33 is mixed. When the seawater 2a passes under energization from an electric power source 34, the seawater 2a is capable of being heated to a temperature difference between the body of the gold collecting unit 31 and the seawater 2a, which is equal to or higher than at least 7° C.

In use of the gold collecting unit 31, in order to facilitate extraction of metal, the ceramic body is energized so that a temperature of the ceramic body is brought to a temperature equal to or higher than 7° C. as compared with the seawater 2a. If the seawater 2a passes through the gold collecting unit 31, gold is collected within the ceramic body. Although an amount of collection or a collecting quantity is small, collection of gold of the order of 1 gram can be expected by treatment of a plenty of seawater 2a, for example, treatment of the seawater 2a of a unit of 1000 tons. At the same time, collection of manganese can also be expected.

In case where the water treatment apparatus described above is used, intended purification treatment can be achieved by the purification step A and the high purification step B if the treatment objective water 2 is not so much contaminated. In case where waterwork feed water is used as the treatment objective water 2 to produce super pure water, intended purification treatment will also be sufficient with purification treatment by the purification step A and the high purification step B.

On the other hand, in case where underground water or industrial water, or waterwork feed water is used as the treatment objective water 2 to produce super pure water for semiconductors, or in case where seawater is used and is desalination-treated, the highly high purification step C is combined with the purification step A whereby the treatment objective water 2 can efficiently be purification-treated so that it is possible to produce fresh water or super pure water for the semiconductors.

The gold collecting step D should be used for collecting gold.

In any case, the precision filter 19 and the ion-exchange resin tower 20 of the high purification step B, or the precision filter units 25 and 26 and the ion-exchange resin tower 20 of the highly high purification step C efficiently achieve super pure water treatment by synergism with the plurality of ozone supply units 10, 11 and 12, the inorganic filtering unit 16 and the activated-carbon filtering unit 17 serving as filtering units, the ultraviolet-ray irradiating unit (first ultraviolet-ray irradiating unit) 18 and the like, which are arranged in the purification step A in a previous step.

Moreover, also the reverse osmosis membrane 23 which is used in the highly high purification step C efficiently achieves intended super pure water treatment by synergism with the above-described other various purification units, not by mere combination of the ultraviolet-ray irradiation unit 18. The fact that these purification treatments can efficiently be achieved as a whole can be executed on the basis of the technique which is capable of injecting a plenty of ozone gases high in concentration into the high-pressure and high-speed water flow, as has previously been proposed by the inventor of the present invention.

Another embodiment will next be described with reference to FIG. 3.

The embodiment illustrates a water treatment apparatus which is suitable for desalination treatment of seawater. An entire system can use, in combination, elements and equipments similar to those illustrated in FIG. 1, and common parts and portions have the last one digit and two digits of the reference numbers of the level of one hundred, which are the same as those of the equipments illustrated in FIG. 1. Duplicated description will be omitted as far as possible.

A saline water tank 101 is provided in which seawater 102a is received as treatment objective water. The saline water tank 101 is provided with a preparatory purification device which includes a pump 50, a sand filtering unit 51 and an ozone supply unit 52. A water flow pipe 103 is connected to the saline water tank 101, and successively connected to a treatment system therefor are a first treatment step 53, a second treatment step 54, a third treatment step 55 and a fourth treatment step 56. Lastly, a fresh water tank 57 is connected to the treatment system. The first treatment step 53 and the second treatment step 54 cooperate with each other to form a "pretreatment step" with respect to the third treatment step 55, and the fourth treatment step 56 forms a "post-treatment step" with respect to the third treatment step 55. A recirculation water flow pipe 106 branches off from the water flow pipe 103 after the second treatment step 54 so that treated water can be recirculated into the saline tank 101.

The first treatment step 53 is provided with a first pump 108, a sand filtering unit 116, a first ozone supply unit 110, a flow meter 58, a first ozone reaction tank 113, an activated-carbon filtering unit 117 and a precision filter 59. The first ozone supply unit 110 is formed by an ozonizer 60, an ozone injection unit (ejector) 61 and a mixing unit (magnetic mixer) 62 for mixing the ozone and the treatment water with each other. The precision filter 59 intends to remove impurities equal to or less than 5 µm, and is equivalent to or corresponds to the precision filter 25a of the previously described embodiment in view of ability.

The second treatment step 54 is provided with a tank 63 in which treatment liquid is temporarily reserved or stored, a second pump 109, a sand filtering unit 116, a second ozone supply unit 111, a flow meter 64, an activated-carbon filtering unit 117 and a precision filter unit 65. The second ozone supply unit 111 is similar to the previously described first ozone supply unit 110, and common parts will be designated by the same reference numerals. The precision filter unit 65 is formed by a first filter 65a for removing impurities equal to or less than 5 µm, and a second filter 65b for removing impurities equal to or less than 1 µm. In view of ability, the first and second filters correspond respectively to the first filter 25a and the second filter 25b of the previous embodiment.

The third treatment step 55 is formed by a reverse osmosis membrane unit 123 which is the most important for desalination treatment. In the illustrated example, five (5) reverse osmosis membrane units are used. However, the number of the units can freely be increased and decreased in conformance with a treatment quantity.

The fourth treatment step 56 is provided with a tank 66 in which treatment liquid is temporarily stored or reserved, a third pump 67, a sand filtering unit 116, a third ozone supply unit 112, a flow meter 68, an activated-carbon filtering unit 117, a precision filter 69 and an ultraviolet-ray irradiating unit 124. The third ozone supply unit 112 is similar to the previously described first ozone supply unit 110, and common parts will be designated by the same reference numerals. The precision filter 69 removes impurities equal to or less than 1 µm, and corresponds to the fourth filter 26a of the previous embodiment in view of ability.

Figure 3:
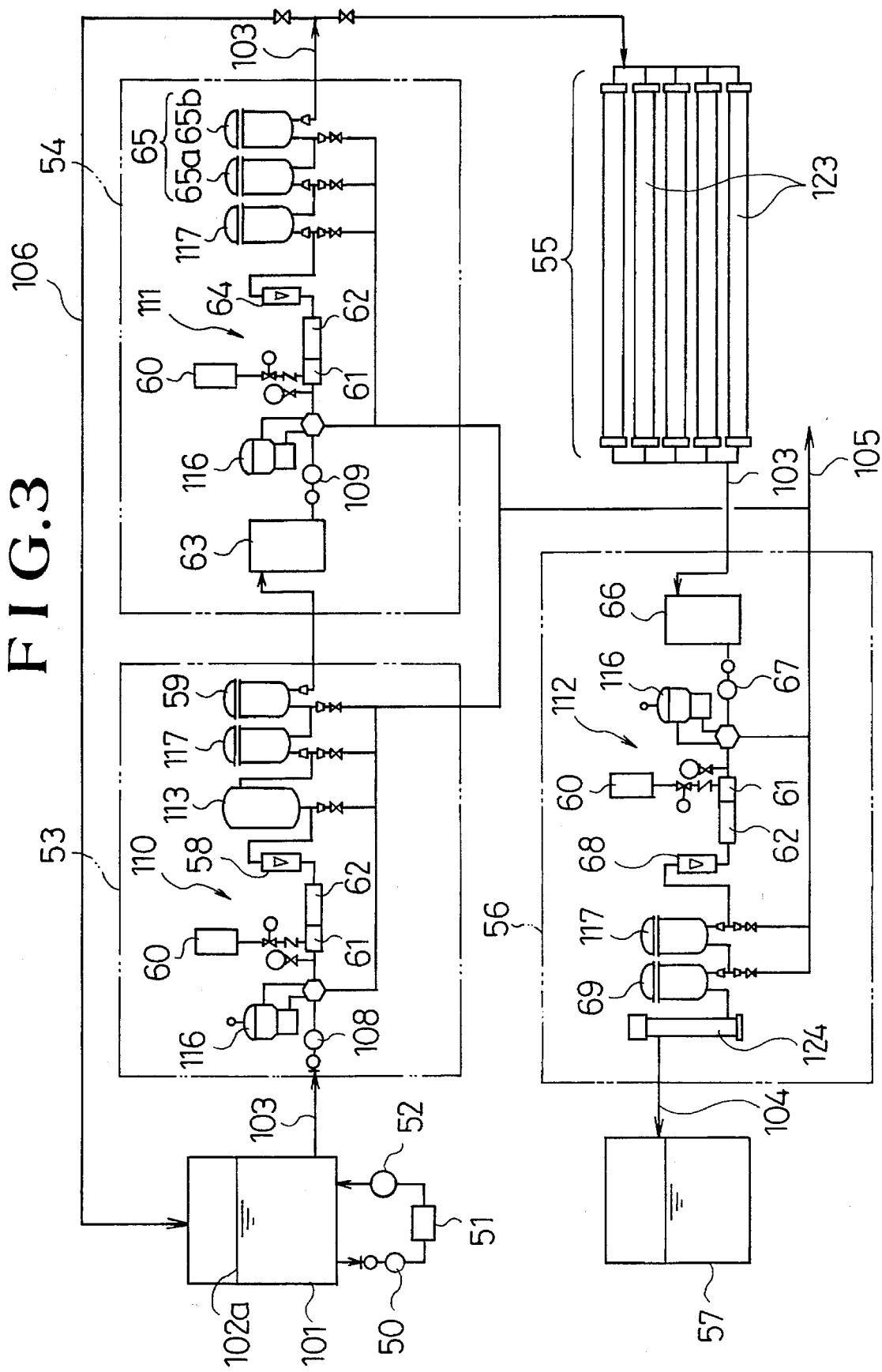
FIG. 3 is a view of entire steps, showing a second embodiment of a water treatment apparatus.

An apparatus system for efficiently desalination-treating seawater is combined with the water treatment apparatus and with the water treatment method using the apparatus, illustrated in FIG. 3. Substantial desalination treatment is executed by the reverse osmosis unit 123 which is arranged in the third treatment step 55. However, by the whole or entire synergistic effect due to the fact that the first treatment step 53 and the second treatment step 54, which serve as a "pretreatment step" of the desalination step, and the fourth treatment step 56, which serves as a "post-treatment" of the desalination step, are combined with the reverse osmosis membrane unit 123, it is possible to achieve efficient desalination treatment at the third treatment step 55. In this connection, if seawater 102a is heated by an adequate heater 120 at any one of the equipments and the steps, prior to the seawater 102a being led to the reverse osmosis membrane unit 123, so as to be brought to a temperature equal to or above 7° C., it is preferable that decomposition of salinity is promoted or accelerated.

Other respects are substantially similar to those of the embodiment illustrated in FIG. 1, and the duplicated description thereof will be omitted.

What is claimed is:

1. A water treatment method comprising the steps of:
   flowing treatment objective water through a first portion of a treatment system comprising an ozone supply unit, a filtering unit and an ultraviolet-ray irradiating unit, to purify the treatment objective water;
   flowing the treatment objective water through a second portion of the treatment system having a precision filter and an ion-exchange resin tower;
   treating said treatment objective water within said first portion of said treatment system by injecting ozone from said ozone supply unit, filtering the water with said filtering unit and irradiating the water with the ultraviolet-ray irradiating unit, to form a clean water;
   treating said clean water within said second portion of the treatment system by filtering out small impurities with said precision filter and removing ions with said ion-exchange resin tower, to form a super pure water;
   reducing an amount of dissolved oxygen in said clean water; and
   enabling said treatment objective water to flow out to a location on the outside of the treatment system, from a final step, as one of super pure water and potable water which can immediately be used;
   wherein said method further includes the step of flowing said treatment objective water through a third portion of the treatment system comprising a reverse osmosis membrane and an ultraviolet-ray irradiating unit provided downstream of said ozone supply unit, to treat said treatment objective water.

2. A water treatment method according to claim 1, wherein said treatment objective water is seawater, and further comprising the step of removing impurities and salinity from the seawater using the reverse osmosis membrane.

3. A water treatment method comprising the steps of:
   flowing treatment objective water through a first portion of a treatment system comprising an ozone supply unit, a filtering unit and an ultraviolet-ray irradiating unit, to purify the treatment objective water;
   flowing the treatment objective water through a desalination portion of the treatment system comprising a precision filter, a reverse osmosis membrane, and an ion-exchange resin all of which are located downstream of said first portion;

treating the treatment objective water within said desalination portion to form potable water by removing impurities and salinity from the treatment objective water; and flowing said potable water out to a location on the outside of the treatment system.

4. A water treatment apparatus comprising:

a treatment system having treatment objective water flowing therethrough, said treatment system comprising an ozone supply unit, a filtering unit and a first ultraviolet-ray irradiating unit, to purify the treatment objective water;

said treatment system further comprising an ozone reaction tank receiving treatment objective water from said ozone supply unit; and said treatment system further comprising a high purifying portion connected to an output portion of said first ultraviolet-ray irradiating unit, said high purifying portion including a first precision filter, a reverse osmosis membrane, a second ultraviolet-ray irradiating unit, a second precision filter, and an ion-exchange resin tower, wherein said high purifying portion is located downstream of said ozone supply unit and includes means for recirculating at least a portion of said treatment objective water into said treatment system upstream of said first ultraviolet-ray irradiating unit whereby treatment objective water is recirculated through said first ultraviolet-ray irradiating unit.

5. A water treatment apparatus according to claim 4, including a gold collecting unit located between said first precision filter and said reverse osmosis membrane.

6. A water treatment apparatus comprising:

a treatment system having treatment objective water flowing therethrough, said treatment system comprising an ozone supply unit, a filtering unit and a first ultraviolet-ray irradiating unit, to purify the treatment objective water;

said treatment system further comprising an ozone reaction tank operatively connected downstream from said ozone supply unit to receive treatment objective water from said ozone supply unit; and said treatment system further comprising a high purifying portion connected to an output portion of said first ultraviolet-ray irradiating unit, said high purifying portion including a first precision filter, a reverse osmosis membrane, a second ultraviolet-ray irradiating unit, a second precision filter, and an ion-exchange resin tower, said high purifying portion including means for recirculating at least a portion of said treatment objective water into said treatment system upstream of said first ultraviolet-ray irradiating unit whereby treatment objective water is recirculated through said first ultraviolet-ray irradiating unit;

wherein a gold collecting unit is provided between said second precision filter and said reverse osmosis membrane, said gold collecting unit having a plurality of passage bores through which seawater flows into an interior of said gold collecting unit, and a ceramic body which is capable of being heated by energization.

7. A water treatment apparatus comprising:

a treatment system having a first purification portion, a second purification portion, and a third purification portion, said first purification portion including:

means for supplying ozone gas of high concentration to treatment objective water, ozone reaction tank means operatively connected to said ozone supply means for receiving treatment objective water from said ozone-gas supply means, means operatively connected to said ozone reaction tank means for filtering treatment objective water received from said ozone reaction tank means to remove inorganic matters from said treatment objective water and to absorb and remove oxidizing matters and organic matters, and means operatively connected to said filtering means for irradiating treatment objective water from said filtering means with ultraviolet radiation to sterilize bacteria and decompose organic matters to form clean water, said ozone-gas supply means and said ozone reaction tank means together applying an oxidized sterilization action, a decolorization action and a deodorization action due to ozone, to the treatment objective water;

said second purification portion including precision filter means for removing residue of the bacteria and the organic matters from said clean water, which are sterilized and decomposed by said ultraviolet-ray irradiating means, and ion-exchange resin tower means for removing ions from said clean water; and said third purification portion connected to said second purification portion downstream of said first purification portion, said third purification portion including reverse osmosis membrane means, ultraviolet-ray irradiating means and precision filter means for removing residue from the treatment objective water;

wherein said treatment objective water passes through said ion-exchange resin tower means of said second purification portion to remove ions from said treatment objective water.

8. A water treatment apparatus according to claim 7, wherein said third purification portion further includes means located between said precision filter and said reverse osmosis membrane, for collecting gold from said treatment objective water.

9. A water treatment apparatus according to claim 7, wherein said ozone supply means includes first, second and third ozone supply units, and said ozone reaction tank means includes first, second and third ozone reaction tanks, said first, second, and third ozone reaction tanks respectively receiving from said first, second and third ozone supply units treatment objective water with said ozone gas therein.

10. A water treatment apparatus according to claim 7, wherein said filtering means includes an inorganic filtering unit and an activated-charcoal filtering unit.

11. A water treatment apparatus according to claim 10, wherein said inorganic filtering unit is a sand filtering unit.

12. A water treatment apparatus according to claim 10, wherein a combination of coconut husk, coal and petroleum are present in said activated-charcoal filtering unit for removing oxidizers and organic matters from said treatment objective water.

13. A water treatment apparatus according to claim 7, wherein said precision filter means of said third purification portion includes means for removing impurities at most equal to 1 μm.

14. A water treatment apparatus according to claim 13, wherein said precision filter means of said third purification portion includes a plurality of precision filters connected in series to each other.

15. A water treatment apparatus according to claim 7, wherein said ion-exchange resin tower means includes an ion-exchange resin which is a strong acidic cation exchange resin.

16. A water treatment apparatus according to claim 7, wherein said ion-exchange resin tower means includes an ion-exchange resin which is a strong basicity anion exchange resin.

17. A water treatment apparatus according to claim 7, including chromaticity meter means and electricity conductivity measuring means which are connected in series to said ion-exchange resin tower means.

18. A water treatment apparatus according to claim 7, wherein said precision filter means of said third purification portion comprises a first filter for removing impurities of 5 μm from said treatment objective water, a second filter for removing impurities of 1 μm from said treatment objective water and a third filter for removing impurities of 0.1 to 0.6 μm from said treatment objective water.

19. A water treatment apparatus according to claim 18, wherein said precision filter means of the third purification portion further comprises a fourth filter for removing impurities of 1 μm and a fifth filter for removing impurities of 0.1 to 0.6 μm, said fourth filter and said fifth filter being arranged downstream of said ultraviolet-ray irradiating means.

20. A water treatment apparatus according to claim 7, wherein said reverse osmosis membrane means is provided immediately downstream from said precision filter means of said third purification portion.

21. A water treatment apparatus according to claim 7, wherein said reverse osmosis membrane means is a polyamide membrane.

22. A water treatment apparatus comprising a treatment system having a first purification portion, a second purification portion, and a third purification portion, said first purification portion including:
means for supplying ozone gas of high concentration to treatment objective water,
ozone reaction tank means operatively connected to said ozone supply means for receiving treatment objective water from said ozone-gas supply means,
means operatively coupled to said ozone reaction tank means for filtering the treatment objective water received from said ozone reaction tank means to remove inorganic matters from said treatment objective water and to absorb and remove oxidizing matters and organic matters, and
means operatively coupled to said filtering means for irradiating treatment objective water from said filtering means with ultraviolet radiation to sterilize bacteria and decompose organic matters to form clean water,
said ozone-gas supply means and said ozone reaction tank means together applying an oxidized sterilization action, a decolorization action and a deodorization action due to ozone, to the treatment objective water;
said second purification portion including precision filter means for removing residue of the bacteria and the organic matters from said clean water, which are sterilized and decomposed by said ultraviolet-ray irradiating means, and ion-exchange resin tower means for removing ions from said clean water; and
said third purification portion connected to said second purification portion downstream of said first purification portion, said third purification portion including reverse osmosis membrane means, ultraviolet-ray irradiating means and precision filter means for removing residue from the treatment objective water;
wherein said treatment objective water passes through said ion-exchange resin tower means of said second purification portion to remove ions from said treatment objective water;
wherein said third purification portion further includes means located between said precision filter and said reverse osmosis membrane, for collecting gold from said treatment objective water, said gold collecting means comprises a power source, a ceramic body, and means connected to said power source for enabling said ceramic body to be heated to such a temperature that a temperature difference between said ceramic body and the treatment objective water is at least equal to 7° C.

23. A seawater treatment apparatus comprising:
a first treatment portion including first means for supplying ozone to said seawater, first tank means within which said seawater reacts with said ozone supplied by said first ozone supply means, and first filtering means for filtering said seawater from said first tank means;
a second treatment portion including second means for supplying ozone to said seawater from said filtering means of said first treatment portion, second tank means within which said seawater reacts with said ozone supplied by said second ozone supply means, and second filtering means for filtering said seawater from said second tank means;
a third treatment portion including reverse osmosis membrane means through which said seawater from said second filtering means passes; and
a fourth treatment portion including third means for supplying ozone to the seawater from said reverse osmosis membrane means of said third treatment portion, third tank means within which said seawater reacts with said ozone supplied by said third ozone supply means, third filtering means for filtering said seawater from said second tank means, and means for irradiating ultraviolet-rays to the seawater from said third filtering means.

24. 4A water treatment apparatus according to claim 23, further including a purification means for filtering impurities from, and supplying ozone to, said seawater, said purification means being connected to said first treatment portion with said first treatment portion located between said purification means and said second treatment portion.

25. A water treatment apparatus according to claim 24, wherein said purification means includes tank means for receiving therein said seawater, pump means connected to said tank means, means for filtering the seawater from said pump means, and means for supplying ozone to the seawater from said filtering means.

26. A water treatment apparatus according to claim 25, wherein said filtering means of said purification means is a sand filtering unit.

27. A water treatment apparatus according to claim 23, wherein said first ozone supply means includes an ozonizer, an ozone injection unit and means for mixing the ozone and the seawater with each other.

28. A water treatment apparatus according to claim 27, wherein said mixing means is a magnetic mixer.

29. A water treatment apparatus according to claim 23, wherein said second filtering means includes a first filter for removing impurities at least equal to 5 μm.

30. A water treatment apparatus according to claim 29, wherein said second filtering means includes a second filter for removing impurities at least equal to 1 μm.

31. A water treatment apparatus according to claim 23, wherein said second filtering means includes means for removing impurities at least equal to 1 μm.

32. A water treatment apparatus according to claim 23, wherein means are provided upstream of said reverse osmosis membrane means, for heating said seawater to a temperature difference of at least 7° C.

33. A water treatment apparatus comprising:

a treatment system comprising a first portion, a second portion, and a third portion;

means for flowing treatment objective water through said first portion of the treatment system, said first portion comprising an ozone supply unit, a filtering unit and an ultraviolet-ray irradiating unit, to purify the treatment objective water;

means for flowing the treatment objective water through said second portion of the treatment system, said second portion having a precision filter and an ion-exchange resin tower;

means for treating said treatment objective water within said first portion of said treatment system by injecting ozone from said ozone supply unit, filtering the water with said filtering unit and irradiating the water with the ultraviolet-ray irradiating unit, to form a clean water;

means for treating said clean water within said second portion of the treatment system by filtering out small impurities with said precision filter and removing ions with said ion-exchange resin tower, to form a super pure water;

means for reducing an amount of dissolved oxygen in said clean water; and means for enabling said treatment objective water to flow out to a location on the outside of the treatment system as potable water which can immediately be used;

wherein said apparatus further includes means for flowing said treatment objective water through said third portion of the treatment system, said third portion comprising a reverse osmosis membrane and an ultraviolet-ray irradiating unit provided downstream of said ozone supply unit, to treat said treatment objective water.

34. A water treatment apparatus according to claim 33, wherein said treatment objective water is seawater, and said reverse osmosis membrane includes means for removing salinity from said seawater.

35. A water treatment apparatus according to claim 34 further comprising means for removing gold from said treatment objective water, said gold removing means being provided downstream from said reverse osmosis membrane.

36. A water treatment apparatus according to claim 33, further comprising a chromaticity meter and an electric-conductivity meter connected to an output portion of said apparatus.

37. A water treatment apparatus comprising:

a treatment system comprising a first portion and a desalination portion;

means for flowing treatment objective water through said first portion of the treatment system, said first portion comprising an ozone supply unit, a filtering unit and an ultraviolet-ray irradiating unit, to purify the treatment objective water;

means for flowing the treatment objective water through said desalination portion of the treatment system, said desalination portion comprising a precision filter, a reverse osmosis membrane, and an ion-exchange resin tower all of which are located downstream of said first portion;

means for treating the treatment objective water within said desalination portion to form potable water by removing impurities and salinity from the treatment objective water; and means for flowing said potable water out to a location on the outside of the treatment system.

* * * * *